United States Patent [19]  
Grollier

[11] Patent Number: 4,834,768  
[45] Date of Patent: May 30, 1989

[54] DYEING COMPOSITIONS FOR KERATIN FIBERS BASED ON DIRECT DYESTUFFS AND XANTHANE GUMS

[75] Inventor: Jean F. Grollier, Paris, France

[73] Assignee: L'Oreal, Paris, France

[21] Appl. No.: 133,172

[22] Filed: Dec. 11, 1987

Related U.S. Application Data

[63] Continuation of Ser. No. 873,449, Jun. 6, 1986, abandoned, which is a continuation of Ser. No. 624,254, Jun. 25, 1984, abandoned.

[30] Foreign Application Priority Data

Jun. 27, 1983 [LU] Luxembourg .............................. 84875

[51] Int. Cl.⁴ .......................... A61K 7/13; A61K 9/12; D06P 3/32
[52] U.S. Cl. ............................................ 8/405; 8/406; 8/414; 8/415; 8/416; 8/426; 8/428; 424/47; 514/782; 514/937; 514/944
[58] Field of Search .................. 8/405, 414, 415, 426, 8/428; 514/782

[56] References Cited

U.S. PATENT DOCUMENTS

| | | | |
|---|---|---|---|
| 3,168,442 | 2/1965 | Brunner et al. | 8/415 |
| 3,349,077 | 10/1967 | Schweiger | 260/209 |
| 3,632,290 | 1/1972 | Tucker et al. | 8/10.1 |
| 3,647,350 | 3/1972 | Galerne | 8/405 |
| 3,659,026 | 4/1972 | Schuppner | 424/363 |
| 3,717,452 | 2/1973 | Gibsen et al. | 424/363 |
| 3,819,827 | 6/1974 | Berger et al. | 424/70 |
| 3,906,091 | 9/1975 | Zuiak et al. | 424/62 |
| 3,973,900 | 8/1976 | Husemeyer et al. | 8/415 |
| 4,278,657 | 7/1981 | Tezuka et al. | 424/363 |
| 4,297,100 | 10/1981 | Koci et al. | 8/527 |
| 4,419,101 | 12/1983 | Bugaut et al. | 8/415 |
| 4,470,826 | 9/1984 | Bugaut et al. | 8/414 |

OTHER PUBLICATIONS

Dorfel, K., Tenside(4):119–121 (Apr. 4, 1966) English Summary.
Racciato, J. S., "Printing Cationic Dyes with Xanthan Gum or Algin", Textile Chemist & Colorist 11,(2):46/31–50/35 (Feb. 1979).

Primary Examiner—Dale R. Ore
Attorney, Agent, or Firm—Fleit, Jacobson, Cohn & Price

[57] ABSTRACT

A dyeing composition for the direct coloring of the hair, containing at least one direct dyestuff, and at least one xanthane gum is disclosed.

11 Claims, No Drawings

DYEING COMPOSITIONS FOR KERATIN FIBERS BASED ON DIRECT DYESTUFFS AND XANTHANE GUMS

This application is a continuation, of application Ser. No. 873,449, filed June 6, 1986 now abandoned, which is a continuation of application Ser. No. 624,254, filed June 25, 1984, now abandoned.

The present invention relates to dyeing compositions for keratin fibres, in particular for colouring human hair, based on direct dyestuffs and xanthane gums.

Keratin fibres such as human hair may be coloured by means of so-called "direct" dyestuffs, which are capable on their own of colouring the keratin fibres.

The dyeing compositions generally used in direct colouring contain at least one direct dyestuff and at least one thickener in a cosmetically acceptable medium.

Thickeners which are frequently used in direct colouring compositions are vegetable thickeners such as sodium alginate, gum arabic, starch, and cellulose derivatives like hydroxyethylcellulose, sodium carboxymethylcellulose, hydroxybutylcellulose and methylcellulose, synthetic thickeners such as acrylic polymers like the sodium salt of polyacrylic acid, and crosslinked polyacrylic acids like the products sold under the names Carbopol 941 and Carbopol 934, higher fatty alcohols, fatty acids, and mineral compounds such as silica, colloidal magnesium aluminium silicate, and clays like bentonite.

However, the dyeing compositions of the state of the art have a number of disadvantages because of the nature of the thickeners used. If these compositions are only slightly thickened, it is virtually impossible to localize them on the hair during application, and, due to the time necessary for colouring, the compositions tend to run onto the forehead and face and can create undesirable marks on the skin and sometimes even on the clothes.

These disadvantages are all the more troublesome since the temperature generally increases from 25 up to about 45° C., either because of the environmental temperature conditions (seasons, countries, temperature of the hair salon) or because these compositions are applied under a hood.

If these compositions are thickened to a greater extent, they are difficult to spread on the hair, irrespective of which of the above mentioned thickeners is used. They may also be difficult to remove on rinsing, as is the case with pyrogenic silica, and are thus unsuitable for cosmetic use.

Moreover, the increase from ambient temperature to about 45° C. tends to fluidize these compositions. This fluidization is irreversible and again presents the problem of localizing the dyeing composition on the hair. Furthermore, the fluidization destabilizes the emulsion forming the support, which results in precipitation of the dyestuff or dyestuffs on cooling and in a modification of the final hue obtained on the hair.

Another disadvantage is that, although the conventional thickeners are effective in an alkaline medium, they often present problems in an acid medium and some of these thickeners react with the direct dyestuffs and degrade them.

We have discovered that it is possible to overcome these various disadvantages by using xanthane gums as thickeners. The compositions which can be prepared by using xanthane gums are pseudo-plastic and have a viscosity which is substantially independent of the pH and stable up to temperatures of the order of 60° C.

We have further found that the use of xanthane gums in dyeing compositions containing direct dyestuffs makes it possible, unexpectedly, to assist the uptake of the dyestuffs on the keratin fibres, to increase the fastness of the colouration obtained and, finally, to improve the keeping properties of the dyestuffs during storage.

Dyeing compositions based on direct dyestuffs and xanthane gums further have the advantage of being able to be used in a highly thickened form such as a gel capable of being packaged in a tube, which rinses out very well but which, in contrast to the abovementioned compositions of the prior art having a similar viscosity, spreads very easily during application to the hair because it becomes fluid very rapidly on application by virtue of the rate of shear due to manual application.

Furthermore, this highly thickened form has the advantage of not running during the colouring period, because the composition gels instantaneously as soon as the shear tension is relaxed.

The direct colouring compositions according to the invention therefore permit a better localization of the colouration on the hair and make it possible to prevent the unpleasant running of the compositions onto the forehead and face.

In contrast to the known compositions, the emulsion containing the dyestuff or dyestuffs remains stable in a gelled medium, even if the ambient temperature conditions increase above 25° C. and up to about 45° C.

These compositions also have the advantage of being able to be formulated within a very extensive pH range which also includes acid pH values. In particular in the case of dyeing compositions containing nitro compounds and a xanthane gum in an acid medium, a better chemical stability of the dyestuffs is observed, for temperatures of from 25° to 45° C., than in the case where a thickener of the Carbopol type is used.

The present invention therefore provides dyeing compositions for the direct colouring of the hair, containing at least one direct dyestuff and at least one xanthane gum.

The invention also provides a process for the direct colouring of the hair in which a composition containing a xanthane gum is used.

The direct dyestuffs used in the compositions according to the invention are preferably chosen from nitro derivatives of the benzene series, indoamine dyestuffs, diarylmethane and triarylmethane dyestuffs, and xanthene, acridine, azine, azo and anthraquinone dyestuffs. These dyestuffs can contain substituents of acidic, nonionic or basic type.

A particularly preferred embodiment of the invention consists of a dyeing composition containing at least one direct dyestuff of acidic type with a xanthane gum in an alkaline medium.

The direct dyestuffs which are more particularly preferred are nitro derivatives of the benzene series, such as, more particularly, nitrophenylenediamines, nitroanilines, nitrophenols and some nitropolyphenols, basic, acidic and disperse anthraquinone dyestuffs and monoazo and diazo dyestuffs, as well as metalliferous dyestuffs.

Examples of nitro derivatives of the benzene series are: 3-amino-4-hydroxynitrobenzene, 2-amino-5-hydroxynitrobenzene, 2-amino-3-hydroxynitrobenzene, 2-amino-5-N,N-bis-β-hydroxyethylaminonitrobenzene, 2-amino-4-chloro-5-N-β-hydroxyethylaminonitrobenzene, 2-amino-4-methyl-5-N-β-hydroxyethylaminonitrobenzene, 3,4-bis-N-β-hydroxyethylaminonitrobenzene, 2-amino-4-methyl-4-N-β,γ-dihydroxypropylaminonitrobenzene, 2-amino-4-methyl-5-β-aminoethylaminonitrobenzene and 2-amino-4-hydroxynitrobenzene, the following being particularly advantageous: 3,4-diaminonitrobenzene, 2,5-diaminonitrobenzene, 2-amino-5-N-β-hydroxyethylaminonitrobenzene, 2-N-β-hydroxyethylamino-5-N,N-bis-β-hydroxyethylaminonitrobenzene, 2-N-methylamino-5-N,N-bis-β-hydroxyethylaminonitrobenzene, 2-N-methylamino-5-N-methyl-N-β-hydroxyethylaminonitrobenzene, 2-N-β-hydroxyethylamino-5-hydroxynitrobenzene, 3-methoxy-4-N-β-hydroxyethylaminonitrobenzene, 4-nitro-3-methylaminophenoxyethanol, 2-N-β-hydroxyethylamino-5-aminonitrobenzene, 2-N-β-hydroxyethylaminonitrobenzene, 3-amino-4-N-β-hydroxyethylaminonitrobenzene, 3-β-hydroxyethoxy-4-N-β-hydroxyethylaminonitrobenzene, 2-amino-5-N-methylaminonitrobenzene, 2-amino-3-methylnitrobenzene, 2-N-β-hydroxyethylamino-5-β,γ-dihydroxypropoxynitrobenzene, 3-hydroxy-4-N-β-hydroxyethylaminonitrobenzene, 3-hydroxy-4-aminonitrobenzene, 2,5-N,N'-β-hydroxyethylaminonitrobenzene, 2-N-methylamino-4-o-β,γ-dihydroxypropoxynitrobenzene, 2-N-β-aminoethylamino-5-N,N-bis-(β-hydroxyethyl)aminonitrobenzene, 2-N-β-aminoethylamino-4-methoxynitrobenzene and 2-N-β-aminoethylamino-5-β-hydroxyethoxynitrobenzene.

Examples of preferred anthraquinone dyestuffs, some given by their name in the Colour Index, are:

Disperse Violet 4, Disperse Blue 1, Acid Violet 43, Disperse Violet 1, Disperse Red 11, Acid Blue 62 and CI Mordant Red 3 (CI 58005), and methyl[(4-hydroxyanthraquinon-1-ylaminopropyl)methylmorpholinium]sulphate.

Examples of preferred indoamine dyestuffs are:

2-N-β-hydroxyethylamino-5,2'-methoxy-4'-aminoanilino-1,4-benzoquinone, 2-N-β-hydroxyethylamino-5,4'-di-N,N'-β-hydroxyethylaminoanilino-1,4-benzoquinone, N-(2'-chloro-4'-hydroxyphenyl)-3-acetylamino-6-methoxy-1,4-benzoquinoneimine, N-(3'-chloro-4'-methylaminophenyl)-3-ureido-6-methyl-1,4-benzoquinoneimine and N-(4'-N,N-ethylcarbamylmethylaminophenyl)-3-ureido-6-methyl-1,4-benzoquinoneimine.

Acridine orange (Basic Orange 14 according to the Colour Index) is a particularly preferred acridine dyestuff.

Rhodamine B (Basic Violet 10 according to the Colour Index) is a particularly preferred xanthene dyestuff.

Examples of azo dyestuffs, named according to the Colour Index, are:

Disperse Yellow 3, Basic Red 76, Basic Brown 16, Basic Yellow 57, Acid Yellow 36, Food Red 1, Acid Orange 7, Acid Red 88, Food Yellow 3, Acid Red 184, Acid Orange 24, Basic Brown 4, Acid Red 35 (CI 18065) and Disperse Black 5.

Examples of triarylmethane dyestuffs, indicated by their name in the Colour Index, are:

Basic Green 1, Basic Violet 14, Basic Violet 1, Basic Violet 3 and Basic Blue 26.

Basic Red 2 is a preferred azine dyestuff.

The xanthane gums used according to the present invention are generally polysaccharides produced by the fermentation of certain sugars with microorganisms, such as the bacterium *Xanthomonas campestris* and the mutants or variants of this type of bacterium.

These gums generally have a molecular weight of from 1,000,000 to 50,000,000 and a viscosity of from 850 to 1600 cps for an aqueous composition containing 1% of xanthane gum (measured on an LVT type Brookfield viscometer at 60 rpm).

Xanthane gums which are more particularly preferred are KELTROL marketed by KELCO, a 1% aqueous solution of which has a Brookfield LVT viscosity at 60 rpm of 1200 to 1600 cps, Rhodopol 23C marketed by Rhône Poulenc, a 0.3% aqueous solution of which has a Brookfield LVT viscosity at 30 rpm of 450±50 cps, Deuteron XG marketed by Schoner G.m.b.H., a 1% aqueous solution of which has a viscosity of 1200 cps measured on a Brookfield LVT viscometer at 30 rpm, and Actigum CX9 marketed by CECA, a 1% aqueous solution of which has a viscosity of 1200 cps measured on a Brookfield LVT viscometer at 30 rpm.

The xanthane gum is preferably used in the compositions according to the invention in proportions of from 0.2% to 5% and preferably from 0.5 to 3% by weight relative to the total weight of the composition.

The composition can optionally contain other thickeners such as, for example, hydroxyethylcellulose.

The direct dyestuffs are preferablyy used in the compositions according to the invention in proportions of from 0.001 to 5% and preferably of from 0.01 to 3% by weight relative to the total weight of the composition.

The dyeing compositions according to the invention can also contain, in addition to the aqueous vehicle for the direct dyestuff and the xanthane gum defined above, organic solvents which are acceptable from the cosmetic point of view, particularly alcohols such as ethyl alcohol, isopropyl alcohol, benzyl alcohol and phenylethyl alcohol, or glycols or glycol ethers, for example, ethylene glycol and its monomethyl, monoethyl and monobutyl ethers, propylene glycol, butylene glycol, dipropylene glycol and the alkyl ethers of diethylene glycol, for example, the monoethyl ether and monobutyl ether of diethylene glycol, preferably in concentrations of from 0.5 to 20% and more preferably of from 2 to 10% by weight, relative to the total weight of the composition.

One of the preferred embodiments of the invention consists of a dyeing composition for human hair which comprises, in a cosmetically acceptable medium, at least one direct dyestuff, at least one xanthane gum and at least one surface-active agent.

The surface-active agent which can be used in the compositions according to the invention can be anionic, cationic, amphoteric or non-ionic. It is also possible to use mixtures of these surface-active agents. The concentrations are generally from 0.1 to 50% by weight and preferably from 1 to 20% by weight, relative to the total weight of the composition.

Examples of anionic surface-active agents are:

the alkali metal salts, magnesium salts, ammonium salts, amine salts or the alkanolamine salts of the following compounds:

alkyl-sulphates, alkyl-ether-sulphates and ethoxylated or non-ethoxylated alkylamide-sulphates, alkylsulphonates, alkylamidesulphonates and α-olefinesulphonates, and alkyl-sulphoacetates, the alkyl radicals of these compounds preferably having a linear chain of 12 to 18 carbon atoms.

It is also possible to use the abovementioned salts of fatty acids such as lauric, myristic, oleic, ricinoleic, palmitic and stearic acids, acids derived from copra oil or from hydrogenated copra oil, and carboxylic acids of polyglycol ethers.

Examples of cationic surface-active agents are:

fatty amine salts, quaternary ammonium salts such as alkyldimethylbenzylammonium, alkyltrimethylammonium, alkyldimethylhydroxyethylammonium and dimethyldialkylammonium chlorides and bromides and alkylpyridinium salts, and imidazoline derivatives. The alkyl groups of the abovementioned quaternary ammonium derivatives are groups with a long chain preferably having from 12 to 18 carbon atoms.

Amine oxides may also be mentioned among these compounds of cationic type.

Examples of amphoteric surface-active agents are:

alkylamino monopropionates and dipropionates, betaines such as alkylbetaines, N-alkylsulphobetaines and N-alkylaminobetaines, the alkyl radical preferably having up to 22 carbon atoms, and cycloimidinium compounds such as alkylimidazolines.

Examples of non-ionic surface-active agents are:

the condensation products of a monoalcohol, an α-diol, an alkylphenol or an amide with glycidol, such as the compounds of the formula:

$$R-CHOH-CH_2-O-(CH_2-CHOH-CH_2-O)_nH$$

in which R denotes an aliphatic, cycloaliphatic or arylaliphatic radical having from 7 to 21 carbon atoms, and mixtures thereof, it being possible for the aliphatic chains to contain ether, thioether and hydroxymethylene groups, and n is a number from 1 to 10;

the compounds of the formula:

$$R_1O-[C_2H_3O-(CH_2OH)]_mH$$

in which $R_1$ denotes an alkyl, alkenyl or alkylaryl radical having 8 to 22 carbon atoms and m is a number from 1 to 10;

the compounds of the formula:

$$R_2-CO-NH-CH_2-CH_2-O-CH_2-CH_2-O-[CH_2-CHOH-CH_2-O]_pH$$

in which $R_2$ denotes a linear or branched, saturated or unsaturated aliphatic radical, or a mixture of such radicals, which can optionally contain one or more hydroxyl groups, has from 8 to 30 carbon atoms and is of natural or synthetic origin, and p is a number from 1 to 5;

polyethoxylated or polyglycerolated fatty alcohols, alkylphenols or acids having a $C_8$ to $C_{18}$ linear fatty chain; condensation products of ethylene oxide and propylene oxide with fatty alcohols; polyethoxylated fatty amides containing at least 5 mol of ethylene oxide; and polyethoxylated fatty amines.

The dyeing compositions according to the invention can also contain fatty amides such as the monoethanolamines and diethanolamides of acids derived from copra, lauric acid or oleic acid, preferably at concentrations of from 0.05 to 10% by weight.

Compositions according to the invention can also contain adjuvants normally used in cosmetic compositions for hair dyeing, such as perfumes, preservatives, sequestering agents, and opacifiers such as the monostearate and distearate of glycol, of polyethylene glycol and of glycerol.

The pH of the dyeing compositions according to the invention is preferably from 5 to 10.5 and advantageously from 6 to 10.

It may be adjusted with alkaline agents such as monoethanolamine, diethanolamine, triethanolamine, aqueous ammonia, the carbonates of ammonium, potassium or sodium, sodium hydroxide or 2-amino-2-methylpropan-1-ol, or with acidifying agents such as phosphoric, hydrochloric, tartaric, acetic, lactic or citric acid.

The dyeing compositions according to the invention can be in a variety of forms customary for hair dyeing, such as thickened liquids, gelled liquids, foaming creams and gels, and aerosol foams.

The compositions may be applied to natural, permed, coloured or bleached hair. The process according to the invention for dyeing keratin fibres, and in particular human hair, consists essentially in applying a composition such as defined above to the keratin fibres.

According to one method of carrying out the invention, the hair is subjected to a lightening treatment, preferably using an ammoniacal solution of hydrogen peroxide or a solution of hydrogen peroxide containing alkaline agents such as aliphatic or hydroxyaliphatic amines, or using an ammoniacal solution of peroxides or alkali metal per-salts, such as sodium peroxide, potassium peroxide, sodium perborate, sodium percarbonate or urea peroxide, or of addition compounds of hydrogen peroxide and organic compounds, such as melamine perhydrate, and also other products capable of lightening the hair.

The lightening composition is applied to the hair and left for an interval, generally of 5 to 30 minutes, depending on the desired degree of lightening; after this, the hair is washed with water and the dyeing composition according to the invention is applied and left for a sufficient period of time to dye the hair. This period is generally from 15 to 30 minutes at ambient temperature.

The hair is then rinsed and dried.

According to another variant of this process, the lightening composition and the dyeing composition of the invention can be applied simultaneously to the hair to be dyed. After an interval, generally of 15 to 30 minutes, the hair is rinsed and dried.

The compositions according to the invention can also be used in multi-step processes in which at least one of the steps involves the application of direct dyestuffs for dyeing the hair.

The Examples which follow further illustrate the invention.

EXAMPLE 1

The following composition is prepared:

| | |
|---|---|
| 2-N—Methylamino-5-N,N—bis-β-hydroxyethyl-aminonitrobenzene | 0.8 g |
| 3-Methoxy-4-N—β-hydroxyethylaminonitrobenzene | 0.15 g |
| 2-Amino-4-methyl-5-N—β-hydroxyethylamino-nitrobenzene | 0.02 g |
| Extra celliton blue sold by BASF (corresponds to CI 64500 - Disperse Blue 1) | 0.1 g |
| Diazo acetoquinone black BSNZ 1350 sold by PCUK (corresponds to Disperse Black 5) | 0.1 g |
| Lauric diethanolamide | 1.5 g |
| Lauric acid | 2.0 g |
| Propyl parahydroxybenzoate | 0.05 g |

| | |
|---|---|
| Methyl parahydroxybenzoate | 0.1 g |
| Ethylene glycol monoethyl ether | 5.0 g |
| Xanthane gum sold under the name Deuteron XG by SCHONER G.m.b.H. | 1.0 g |
| Monoethanolamine | q.s. pH 9.5 |
| Demineralized water | q.s. 100 g |

This composition is in the form of a gelled liquid.

This composition is applied for 30 minutes to light chestnut hair with red highlights, and does not run. After rinsing, the hair is dyed in a natural light chestnut hue. In particular, the red highlights have disappeared.

EXAMPLE 2

The following composition is prepared:

| | |
|---|---|
| 2-N—Methylamino-5-N—methyl-N—β-hydroxy-ethylaminonitrobenzene | 0.25 g |
| 2-N—β-Hydroxyethylamino-5-hydroxynitro-benzene | 0.01 g |
| 2-N—Methylamino-4-β-hydroxyethoxynitro-benzene | 0.10 g |
| 2-N—β-Hydroxyethylamino-5-β,γ-dihydroxy-propoxynitrobenzene | 0.02 g |
| Violet 14 447 (corresponding to Disperse Violet 1) | 0.05 g |
| Lauric diethanolamide | 2 g |
| Lauric acid | 1.5 g |
| Propyl parahydroxybenzoate | 0.05 g |
| Methyl parahydroxybenzoate | 0.10 g |
| Diethylene glycol monobutyl ether | 5 g |
| Xanthane gum sold under the name Rhodopol 23C by Rhone Poulenc | 1.5 g |
| 2-Amino-2-methylpropan-1-ol | q.s. pH 8.5 |
| Demineralized water | q.s. 100 g |

This composition is in the form of a gelled liquid.

This composition is applied to deep blond hair. After an interval of 25 minutes, followed by rinsing, this gives hair possessing mahogany brown highlights.

EXAMPLE 3

The following composition is prepared:

| | |
|---|---|
| 2-Amino-5-N—β-hydroxyethylaminonitrobenzene | 0.30 g |
| 2-Amino-5-N—methylaminonitrobenzene | 1.10 g |
| 2-Amino-3-methylnitrobenzene | 0.6 g |
| 3-Hydroxy-4-N—β-hydroxyethylaminonitro-benzene | 0.1 g |
| Victoria Blue BSA extra sold by PCUK (corresponds to CI 44045 Basic Blue 26) | 0.05 g |
| Lauric diethanolamide | 4 g |
| Sactipon 286 | 20 g |
| Kathon CG | 0.05 g |
| Xanthane gum sold under the name KELTROL by KELCO | 1 g |
| Dilute sodium hydroxide solution | q.s. pH 8 |
| Demineralized water | q.s. 100 g |

This composition is in the form of a gelled liquid.

This colouring shampoo is applied for 30 minutes to deep chestnut hair. After the colouring period, the hair is rinsed. The hair is then dyed with intense auburn highlights.

EXAMPLE 4

The following composition is prepared:

| | |
|---|---|
| Safranine RAL sold by PCUK (corresponds to CI 50 240 - Basic Red 2) | 0.1 g |
| Rhodamine B extra concentrated, sold by ACNA (corresponds to CI 45170 - Basic Violet 10) | 0.05 g |
| Acridine Orange (corresponds to CI 46005 - Basic Orange 14) | 0.1 g |
| Arianor Garance sold by MORTON (corresponds to CI 12245 - Basic Red 76) | 0.05 g |
| 2-N—β-Aminoethylamino-5-β-hydroxyethoxynitro-benzene | 0.2 g |
| Copra monoethanolamide | 4 g |
| Lauryl alcohol containing 23 mol of ethylene oxide | 4 g |
| Propyl parahydroxybenzoate | 0.05 g |
| Methyl parahydroxybenzoate | 0.1 g |
| Xanthane gum sold under the name Deuteron XG by Schoner G.m.b.H. | 1.0 g |
| Triethanolamine | q.s. pH 9 |
| Demineralized water | q.s. 100 g |

This composition is in the form of a gelled liquid.

This composition is applied for 25 minutes to chestnut hair. After rinsing, the hair possesses intense reddish coppery highlights.

EXAMPLE 5

The following composition is prepared:

| | |
|---|---|
| 2-N—β-Hydroxyethylamino-5-N,N—bis-β-hydroxtethylaminonitrobenzene | 0.05 g |
| 2-Amino-3-hydroxynitrobenzene | 0.20 g |
| N—(2'-Chloro-4'-hydroxyphenyl)-3-acetyl-amino-6-methoxy-1,4-benzoquinoneimine | 0.01 g |
| Lauric diethanolamide | 3.0 g |
| Triethanolamine alkyl-sulphate | 2.0 g |
| Ethylene glycol monoethyl ether | 4.0 g |
| Nipa ester 82121 | 0.1 g |
| Xanthane gum sold under the name Keltrol by KELCO | 1.5 g |
| Monoethanolamine | q.s. pH 9.5 |
| Demineralized water | q.s. 100 g |

This composition is in the form of a gelled liquid.

This composition is applied for 30 minutes to deep blond hair. After rinsing, this hair has matt golden highlights.

EXAMPLE 6

The following composition is prepared:

| | |
|---|---|
| Crystalline Violet SADG sold by PCUK (corresponds to CI 42555 - Basic Violet 3) | 0.05 g |
| Methyl [(4-hydroxyanthraquinon-1-ylamino-propyl)methylmorpholinium]sulphate | 0.20 g |
| 2-Amino-5-N—methylaminonitrobenzene | 0.90 g |
| 3,4-Bis-N—β-hydroxyethylaminonitrobenzene | 0.05 g |
| Copra monoethanolamide | 4.0 g |
| Lauryl alcohol containing 23 mol of ethylene oxide | 4 g |
| Propyl parahydroxybenzoate | 0.05 g |
| Methyl parahydroxybenzoate | 0.10 g |
| Xanthane gum sold under the name Rhodopol 23C by Rhone Poulenc | 1.0 g |
| Triethanolamine | q.s. pH 6.5 |
| Demineralized water | q.s. 100 g |

This composition is in the form of a gelled liquid.

This composition is spread over brown hair. After a colouring period of 30 minutes, the hair is rinsed. This gives hair having strong purple-violet highlights.

EXAMPLE 7

The following composition is prepared:

| | |
|---|---|
| 3-Methoxy-4-N—β-hydroxyethylaminonitrobenzene | 0.1 g |
| 2-N—β-Hydroxyethylamino-5-hydroxynitrobenzene | 0.4 g |
| 2-Amino-5-hydroxynitrobenzene | 0.1 g |
| Lauric diethanolamide | 1.5 g |
| Lauric acid | 2.0 g |
| Propyl parahydroxybenzoate | 0.05 g |
| Methyl parahydroxybenzoate | 0.1 g |
| Ethylene glycol monoethyl ether | 5.0 g |
| Xanthane gum sold under the name Deuteron XG by Schoner G.m.b.H. | 1.0 g |
| Monoethanolamine | q.s. pH 9.5 |
| Demineralized water | q.s. 100 g |

This composition is in the form of a gelled liquid.

When applied for 30 minutes to light chestnut hair, this composition imparts to the hair, after rinsing, reddish coppery highlights.

EXAMPLE 8

The following composition is prepared:

| | |
|---|---|
| 2-Amino-4-hydroxynitrobenzene | 0.15 g |
| 3-Hydroxy-4-aminonitrobenzene | 0.10 g |
| 2-N—β-Hydroxyethylamino-5-β,γ-dihydroxypropoxynitrobenzene | 0.10 g |
| Lauric diethanolamide | 2 g |
| Lauric acid | 1.5 g |
| Propyl parahydroxybenzoate | 0.05 g |
| Methyl parahydroxybenzoate | 0.10 g |
| Diethylene glycol monobutyl ether | 5 g |
| Xanthane gum sold under the name Rhodopol 23C by Rhone Poulenc | 1.5 g |
| 2-Amino-2-methylpropan-1-ol | q.s. pH 8.5 |
| Demineralized water | q.s. 100 g |

This composition is in the form of a gelled liquid.

When applied for 30 minutes to deep blond hair, this mixture imparts, after rinsing, a golden colouration.

EXAMPLE 9

The following composition is prepared:

| | |
|---|---|
| 2-Amino-3-hydroxynitrobenzene | 0.30 g |
| CI MORDANT RED 3 (CI 58005) | 0.05 g |
| 3,4-Bis-N—β-hydroxyethylaminonitrobenzene | 0.10 g |
| Lauric diethanolamide | 4 g |
| Sactipon 286 | 20 g |
| Kathon CG | 0.05 g |
| Xanthane gum sold under the name Keltrol by KELCO | 1 g |
| Dilute sodium hydroxide solution | q.s. pH 8 |
| Demineralized water | q.s. 100 g |

This composition is in the form of a gelled liquid.

When applied for 30 minutes to deep blond hair, it gives coppery hair after rinsing.

EXAMPLE 10

The following composition is prepared:

| | |
|---|---|
| Acid Red 35 (CI 18065) | 0.05 g |
| 2-N—β-Hydroxyethylamino-5-hydroxynitrobenzene | 0.6 g |
| 2,5-N,N'—β-Hydroxyethylaminonitrobenzene | 0.2 g |
| 2-N—Methylamino-5-N,N—bis-β-hydroxyethylaminonitrobenzene | 0.3 g |
| Copra monoethanolamide | 4 g |
| Lauryl alcohol containing 23 mol of ethylene oxide | 4 g |
| Propyl parahydroxybenzoate | 0.05 g |
| Methyl parahydroxybenzoate | 0.1 g |
| Xanthane gum sold under the name Deuteron XG by Schoner G.m.b.H. | 1.0 g |
| Triethanolamine | q.s. pH 9 |
| Demineralized water | q.s. 100 g |

This composition is in the form of a gelled liquid.

When applied for 30 minutes to chestnut hair, this composition imparts to the hair, after rinsing, purple-violet mahogany highlights.

In the preceding examples, the trademarks used correspond to the following products:

| | |
|---|---|
| KATHON CG: | is a mixture of 5-chloro-2-methyl-4-isothiazolin-3-one and 2-methyl-4-isothiazolin-3-one in the presence of a magnesium salt, sold by ROHM and HAAS. |
| SACTIPON 286: | is ammonium lauryl-sulphate sold by LEVER. |
| NIPA ESTER 82121: | is a mixture of methyl, ethyl, propyl, butyl and benzyl parahydroxybenzoates, sold by NIPA LABORATOIRES. |

I claim:

1. A dyeing composition for the direct colouring of human hair which comprises about 0.001 to 5% by weight of an acidic or non-ionic direct dyestuff and 0.2 to 5% by weight of a xanthane gum, said xanthane gum being a polysaccharide produced by the fermentation of a sugar and said xanthane gum having a molecular weight of from 1,000,000 to 50,000,000 and a viscosity in 1% aqueous solution of from 850 to 1600 cps, measured by a Brookfield LVT viscometer at 60 rpm.

2. A composition according to claim 1, which further includes an aqueous cosmetically acceptable medium comprising water or a mixture of water and a solvent, said solvent being present in a proportion of 0.5 to 20% by weight relative to the total weight of the composition, wherein said solvent is selected from the group consisting of an alcohol, glycol, glycol ether, and diethyleneglycol alkylether.

3. A composition according to claim 1, in which the xanthane gum is present in a proportion of 0.5 to 3% by weight relative to the total weight of the composition.

4. A composition according to claim 1, in which the direct dyestuff is selected from the group consisting of
a nitro derivative of the benzene series,
an indoamine dyestuff, and
an acidic or dispersed anthraquinone dyestuff.

5. A composition according to claim 4 in which said nitro derivative is selected from the group consisting of
a nitrophenylenediamine,
a nitroaniline,
a nitrophenol and
a nitropolyphenol.

6. A composition according to claim 1, which contains 0.1 to 50% by weight of a member selected from the group consisting of anionic, cationic, amphoteric, and non-ionic surface-active agents.

7. A composition according to claim 1, which is in a form selected from the group consisting of a thickened liquid, a gelled liquid, a foaming cream, a foaming gel and an aerosol foam.

8. A process for dyeing human hair, comprising:

in a first step, subjecting the hair to a lightening treatment by applying thereto a composition selected from the group consisting of an ammoniacal solution of hydrogen peroxide, a solution of hydrogen peroxide containing aliphatic or hydroxyaliphatic amines, an ammoniacal solution of alkali metal peroxides, persalts or urea peroxide and a mixture of hydrogen peroxide and melamine perhydrate, for a period of 5 to 30 minutes; said composition in an amount effective to lighten the color of the hair;

in a second step, rinsing the hair with water; and in a third step, applying a composition containing in a cosmetically acceptable medium between 0.001 and 5% by weight of a direct dyestuff, and 0.2 to 5% by weight of a xanthane gum, said xanthane gum being a polysaccharide produced by the fermentation of a sugar, and said xanthane gum having a molecular weight of from 1,000,000 to 50,000,000 and a viscosity in a 1% aqueous solution of from 850 to 1600 cps, measured by a Brookfield LVT viscometer at 60 rpm.

9. A process for the direct coloring of human hair, comprising:

applying to said hair a composition comprising in a cosmetically acceptable medium between 0.001 and 5% by weight of a direct dyestuff and 0.2 to 5% by weight of a xanthane gum, said xanthane gum being a polysaccharide produced by the fermentation of a sugar and said xanthane gum having a molecular weight of from 1,000,000 to 50,000,000 and a viscosity in a 1% aqueous solution of from 850 to 1600 cps, measured by a Brookfield LVT viscometer at 60 rpm.

10. The process of claim 9 wherein said direct dyestuff is selected from the group consisting of
   a nitro derivative of the benzene series,
   an indomaine dyestuff,
   a diarylmethane dyestuff,
   a triarylmethane dyestuff,
   a xanthene dyestuff,
   an acridine dyestuff,
   an azine dyestuff,
   an azo dyestuff, and
   an anthraquinone dyestuff.

11. The process of claim 10 wherein
   said nitro derivative is selected from the group consisting of a nitrophenylenediamine, a nitroaniline, a nitrophenol and a nitropolyphenol,
   said anthraquinone dyestuff is selected from the group consisting of basic, acidic and disperse anthraquinone dyestuffs, and
   the azo dyestuff is selected from the group consisting of monoazo, diazo, and metalliferous dyestuffs.

* * * * *